(12) United States Patent
Liao et al.

(10) Patent No.: US 8,865,165 B2
(45) Date of Patent: Oct. 21, 2014

(54) **MONOCLONAL ANTIBODY AGAINST GROUP 2 ALLERGEN OF *DERMATOPHAGOIDES PTERONYSSIUNS*, HYBRIDOMA CELL LINE PRODUCING THEREOF, STRIP, KIT AND METHOD USING SAID MONOCLONAL ANTIBODY FOR DUST MITE ASSAY**

(71) Applicant: Taichung Veterans General Hospital, Taichung (TW)

(72) Inventors: En-Chin Liao, New Taipei (TW); Jaw-Ji Tsai, Taipei (TW)

(73) Assignee: Taichung Veterans General Hospital, Taichung (TW)

( * ) Notice: Subject to any disclaimer, the term of this patent is extended or adjusted under 35 U.S.C. 154(b) by 8 days.

(21) Appl. No.: 13/677,516

(22) Filed: Nov. 15, 2012

(65) Prior Publication Data

US 2013/0143242 A1 Jun. 6, 2013

(30) Foreign Application Priority Data

Nov. 16, 2011 (TW) .............................. 100141862 A

(51) Int. Cl.
*A61K 39/395* (2006.01)
*C07K 16/00* (2006.01)
*C12P 21/08* (2006.01)
*G01N 33/53* (2006.01)
*G01N 33/68* (2006.01)
*C07K 16/18* (2006.01)

(52) U.S. Cl.
CPC ............ *C07K 16/18* (2013.01); *G01N 33/5308* (2013.01); *G01N 33/68* (2013.01); *C07K 2317/34* (2013.01)
USPC .................. 424/130.1; 424/141.1; 424/151.1; 530/387.1; 530/388.1

(58) Field of Classification Search
None
See application file for complete search history.

(56) References Cited

U.S. PATENT DOCUMENTS 6,132,734 A 10/2000 Thomas et al.

FOREIGN PATENT DOCUMENTS

TW 200414904 A 8/2004

*Primary Examiner* — Nora Rooney
(74) *Attorney, Agent, or Firm* — Bacon & Thomas, PLLC

(57) ABSTRACT

This present invention discloses a monoclonal antibody which specifically recognizes and binds to a epitope of group 2 allergen of *Dermatophagoides pteronyssiuns*, usually named Der p 2, and a hybridoma cell line producing thereof. Furthermore, this invention also discloses a strip, kit and method utilizing said monoclonal antibody for the detection of the presence of dust mite allergens and the calculation of dust mite number in the environment.

10 Claims, 8 Drawing Sheets ns, HYBRIDOMA CELL LINE PRODUCING THEREOF, STRIP, KIT AND METHOD USING SAID MONOCLONAL ANTIBODY FOR DUST MITE ASSAY

BACKGROUND OF THE INVENTION

1. Field of the Invention

A present invention discloses a monoclonal antibody against Der p 2, hybridoma cell line producing thereof and test strip, kit and method for dust mite assay.

2. Description of the Related Art

Asthma and allergic rhinitis are the most common airway allergic diseases in Taiwan. Both of them are resulted from the inflammation induced by the interaction between respiratory epithelial cells and allergens. The major allergens include hair of vertebrates, egg, murine urine, poisonous fluid of insect, dust mite, cockroach, shrimp, pollen, peanut and fungal. Therein, the dust mite exhibiting rich and diverse allergens majorly distributes at the food, furniture, interior decoration, bedding, carpet and dust within the indoor environment. Besides, allergens from dust mite are particularly easy to cause allergy of airway and skin. Therefore, dust mite is considered as the major allergen in the interior environment.

Previous reports show that dust mite allergens are divided into 22 groups according to their biological characteristics, molecular weight and binding affinity with immunoglobulin E (IgE). Therein, the major allergens are group 1 and group 2 allergen of *Dermatophagoides pteronyssiuns* (Der p 1 and Der p 2). The IgE in the serum from 75% of the allergic patients exhibits the binding response to Der p 1 and Der p 2. Previous reports also suggested that reduce the concentration of allergens in the environment, especially at the onset time of asthma and allergic rhinitis, could efficiently prevent the occurrence of the allergic diseases.

Der p 1 belongs to enzymatic allergen which is unstable to be applied as the real time indicator. In contrast, Der p 2, a stable non-enzymatic allergen, which exhibits the great correction with the number of dust mite in the environment, is a capable indicator for detecting the concentration of dust mite allergen at home. Allowing patients to detect the number of dust mite and control the allergen concentration at home environment brings more economic profit than pharmaceutical therapy.

Monoclonal antibody technology has been widely applied for rapid detection kit because of its advantages, including high specificity, fast reaction and high sensitivity. However, there are still many uncertainties during the production of monoclonal antibody. Therefore, finding the monoclonal antibody with high specificity is the critical point in the development of detection kit.

U.S. Pat. No. 6,132,734 disclosed the amino acid sequence of Der p 2, but did not reveal the specific epitope of the Der p 2 or the monoclonal antibody against Der p 2. In addition, Taiwan Pub. No. 200414904 disclosed the method for producing the monoclonal antibody, WAN-108, via injecting the allergen protein isolated by gel electrophoresis and immunoblotting into recipient mice. However, the allergenic type, recognized epitope and antibody activity of WAN-108 monoclonal antibody still remained elusive. Accordingly, these previously disclosed dust mite detection technologies still remain to be improved.

SUMMARY OF THE INVENTION

The major propose of this invention is to provide a Der p 2 monoclonal antibody which specifically recognizes and binds to a epitope of Der p 2.

In order to achieve said propose, this invention provides a monoclonal antibody specifically binds to a epitope of Der p 2, which said monoclonal antibody binds to the same epitope as the monoclonal antibody produced by hybridoma cell line C1 and has the same antigen binding site as the monoclonal antibody produced by hybridoma cell line C1.

In order to achieve said propose, this invention also provides a monoclonal antibody specifically binds to a epitope of Der p 2, which said monoclonal antibody binds to the same epitope as the monoclonal antibody produced by hybridoma cell line C4 and has the same antigen binding site as the monoclonal antibody produced by hybridoma cell line C4.

According to the above technical feature, said monoclonal antibody in this invention exhibits the immunological characteristic to recognize and specifically bind to Der p 2.

Another purpose of this invention is going to provide an immortalized hybridoma cell line for the use in producing monoclonal antibody against the epitope of Derp2.

To achieve said purpose, this invention provides an immortalized cell line which produces a monoclonal antibody, wherein said monoclonal antibody specificity binds to the same epitope of Der p 2 as the monoclonal antibody produced by hybridoma cell line C1 and has the same antigen binding site as the monoclonal antibody produced by hybridoma cell line C1.

To achieve said purpose, this invention also provides an immortalized cell line which produces a monoclonal antibody, wherein said monoclonal antibody specificity binds to the same epitope of Der p 2 as the monoclonal antibody produced by hybridoma cell line C1 and has the same antigen binding site as the monoclonal antibody produced by hybridoma cell line C1.

According to the above technical feature, said monoclonal antibody produced by said cell line in this invention exhibits the immunological characteristic to recognize and specifically bind to Der p 2.

Another purpose in this invention is to provide a test strip, kit and method for use in rapidly detection of the dust mite allergens in the environment.

In order to achieve said purpose, this invention provides a test strip for dust mite assay comprises a solid matrix comprising a sample area, a binding area, a flow area and a absorbing area which allows a solution to flow in order, wherein said flow area having a test region and a control region and the distance between said test region and said binding region is shorter than the distance between control region and binding region; a conjugate setting on said binding area with capable of flowing, wherein said conjugate comprising a first antibody and a label wherein said primary antibody is the monoclonal antibody specifically binding to a epitope of Der p 2, which said primary antibody binding to the same epitope as the monoclonal antibody produced by hybridoma cell line C1 and has the same antigen binding site as the monoclonal antibody produced by hybridoma cell line C1 and said primary antibody covalently associate with said label; a secondary antibody fixed on said test region, wherein said secondary antibody is the monoclonal antibody specifically binding to a epitope of Der p 2, which said secondary antibody binds to the same epitope as the monoclonal antibody produced by hybridoma cell line C4 and has the same antigen binding site as the monoclonal antibody produced by hybridoma cell line C4; and a third antibody fixed on said control region and specifically binding to said primary antibody.

To achieve said purpose, this invention provides a dust mite detection kit which comprises said test strip and a sample buffer.

In addition, this invention also provides a method for dust mite assay which comprises (a) putting a sample and a conjugate together to reaction, wherein said conjugate comprising a first antibody and a label wherein said primary antibody is the monoclonal antibody specifically binding to a epitope of Der p 2, which said primary antibody binding to the same epitope as the monoclonal antibody produced by hybridoma cell line C1 and has the same antigen binding site as the monoclonal antibody produced by hybridoma cell line C1 and said primary antibody covalently associate with said label; (b) putting the complex of said conjugate binding with the antigen and a second antibody fixed on a solid matrix together to reaction, wherein said secondary antibody is the monoclonal antibody specifically binding to a epitope of Der p 2, which said secondary antibody binds to the same epitope as the monoclonal antibody produced by hybridoma cell line C4 and has the same antigen binding site as the monoclonal antibody produced by hybridoma cell line C4; and (c) observing color development of said label on said solid matrix.

Upon these described technical features, said test strips, kit and method for dust mite assay utilize said monoclonal antibody which specifically recognizes Der p 2 to perform immunological reaction with the samples collected from the environment to rapidly detect the environmental dust mite allergens.

Another purpose of this invention is going to provide a kit and a method for dust mite assay to detect the allergens and the allergen amount in the environment rapidly and accurately.

To archive said purpose, this invention provides a kit for must mite assay which comprises a primary antibody fixed on a solid matrix which is the monoclonal antibody specifically binding to a epitope of Der p 2, which said primary antibody binds to the same epitope as the monoclonal antibody produced by hybridoma cell line C1 and has the same antigen binding site as the monoclonal antibody produced by hybridoma cell line C1; a secondary antibody which is the polyclonal antibody against Der p 2 or the monoclonal antibody specifically binding to a epitope of Der p 2 which said secondary antibody binds to the same epitope as the monoclonal antibody produced by hybridoma cell line C4 and has the same antigen binding site as the monoclonal antibody produced by hybridoma cell line C4; and a conjugate comprising a third antibody and a label wherein said third antibody specifically binds to said secondary antibody and covalently associates with said label.

In order to achieve said purpose, this invention discloses a method for dust mite assay which comprising (a) putting a sample and a primary antibody fixed on a solid matrix together to reaction, wherein said primary antibody is the monoclonal antibody specifically binding to a epitope of Der p 2, which said primary antibody binding to the same epitope as the monoclonal antibody produced by hybridoma cell line C1 and has the same antigen binding site as the monoclonal antibody produced by hybridoma cell line C1 and said primary antibody covalently associate with said label; (b) putting the complex of said first antibody binding with the antigen and a second together to reaction, wherein said secondary antibody is the polyclonal antibody against Der p 2 or the monoclonal antibody specifically binding to a epitope of Der p 2 which said secondary antibody binds to the same epitope as the monoclonal antibody produced by hybridoma cell line C4 and has the same antigen binding site as the monoclonal antibody produced by hybridoma cell line C4; (c) putting the complex of said first antibody binding with the antigen and said second antibody, and a conjugate together to reaction, which said conjugate comprising a third antibody and a label wherein said third antibody specifically binds to said secondary antibody and covalently associates with said label; and (d) measuring said label on said solid matrix.

Upon said technical characteristics above, this invention provides said kit and method for the use in dust mite assay by utilizing said monoclonal antibody against Der p 2 which performs immunological reaction with the environmental sample for precisely analyzing the presence and the number of dust mite allergen in the environment.

The details about the structure, characteristics, assembling procedure and measuring method of this invention will be further explained in the following text. However, the above mentioned specification is only for detailed description with the examples of the invention and shall not be construed as a limitation of the scope of this invention. Thus, any modification or change without departing from the characteristics of the invention or any equivalent thereof shall be included in the scope of the invention defined in the following claims.

Figure 8:
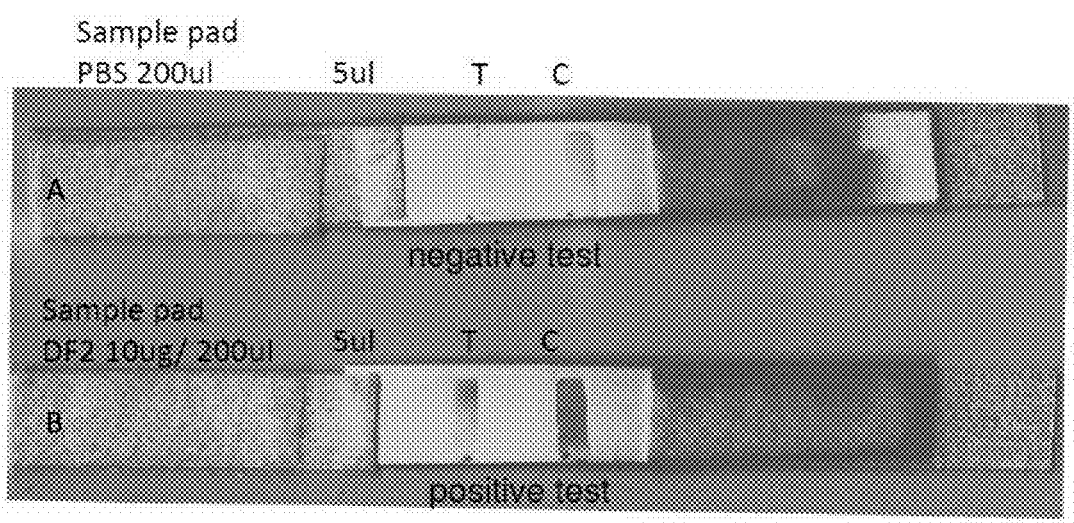

FIG. 8 shows the detection results that adding 200 µl of different samples on the test strip which contains antibody C1 concentration 5 µg/ml within the binding area. Strip A shows that adding PBS onto the test strip. Strip B shows that 10 µg rDer f 2 containing solution added onto the test strip.

Figure 9:
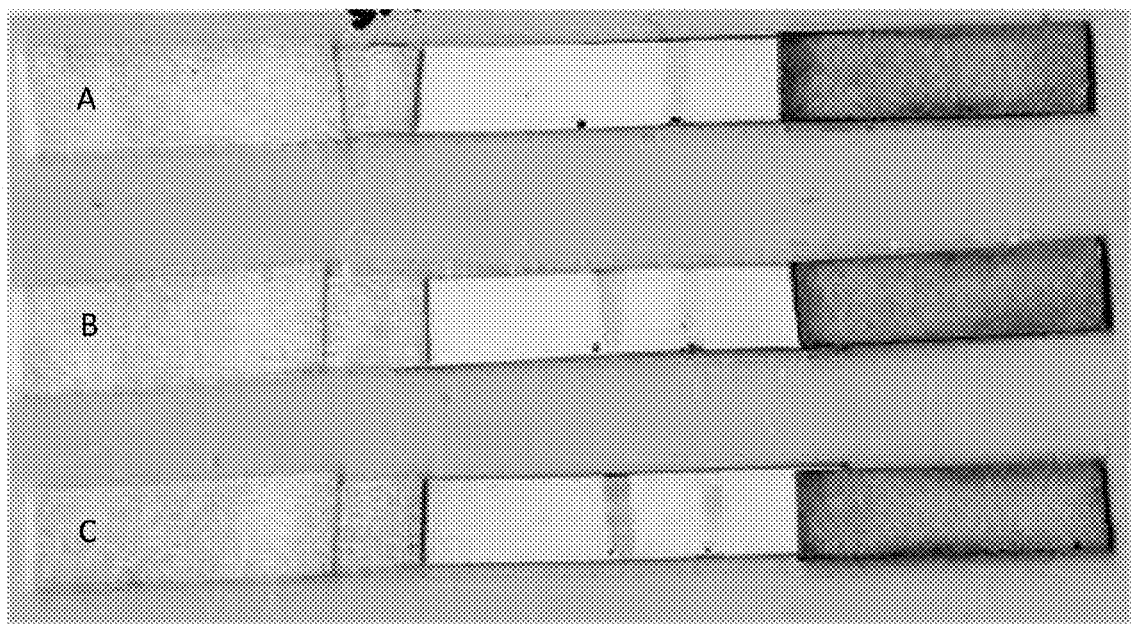

FIG. 9 shows the detection results that adding 100 µl of different samples on the test strip which contains antibody C1 concentration 10 µg/ml within the binding area. Strip A shows that adding PBS onto the test strip. Strip B shows that 1 µg rDer p 2 protein containing solution added onto the test strip. Strip C shows that 10 µg rDer p 2 protein containing solution added into the test strip.

Figure 10:
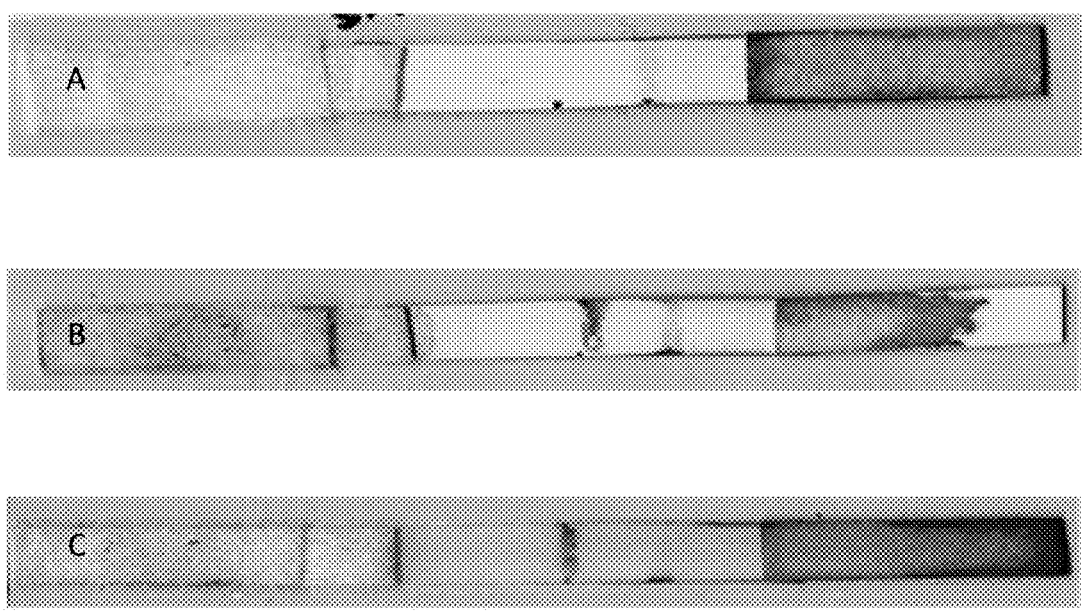

FIG. 10 shows the detection results that adding 100 µl of different samples on the test strip which contains antibody C1 concentration 10 µg/ml within the binding area. Strip A shows that adding PBS onto the test strip. Strip B shows that dust samples from emergency added onto the test strip. Strip C shows that dust samples from duty room at 10 F added onto the test strip.

Figure 11:
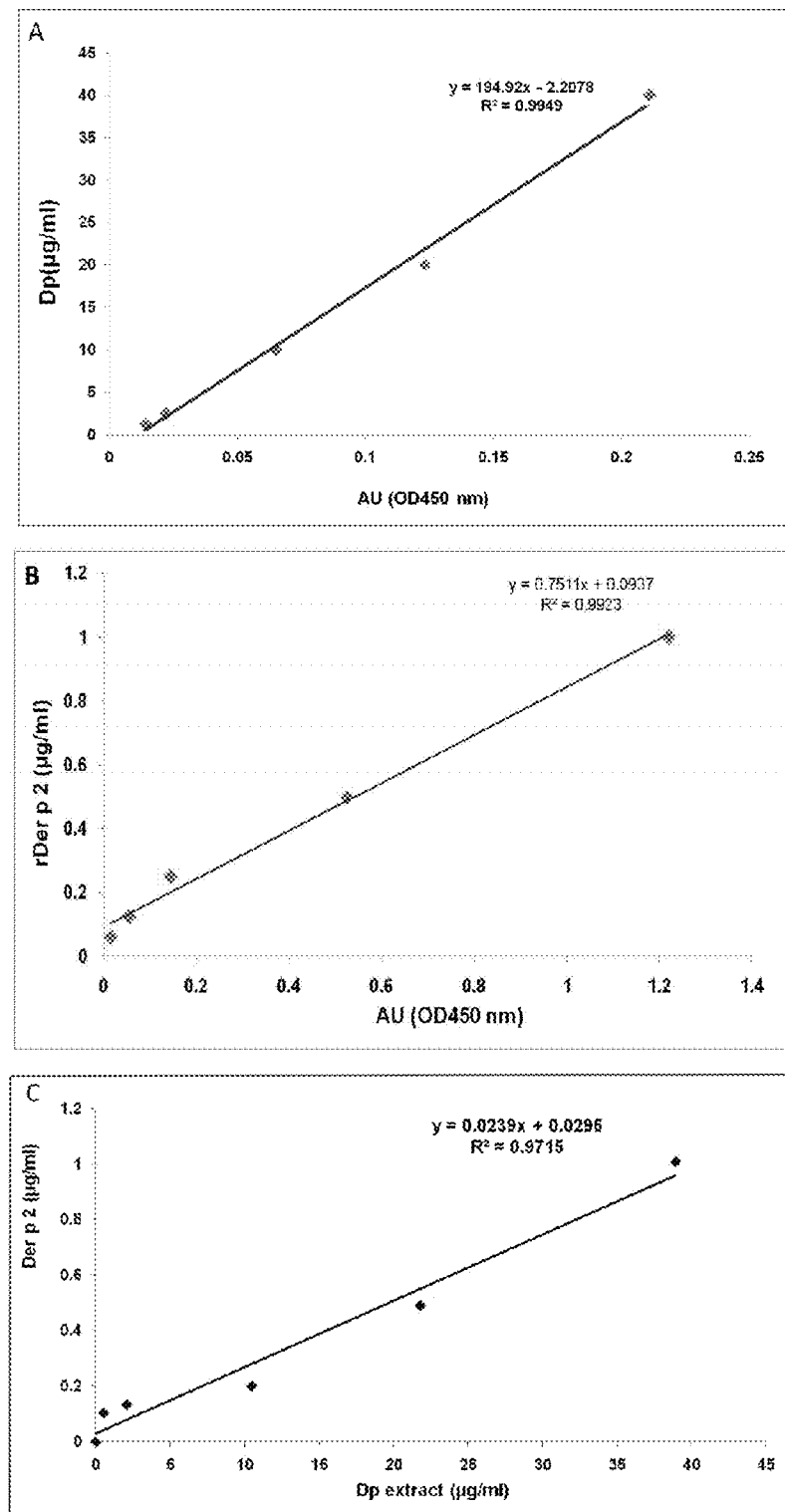

FIG. 11 shows the result of Der p 2 concentration in the crude extract of Dp. The monoclonal antibody was subjected as the capture antibody and the rabbit polyclonal antibody was used as the detection antibody. In addition, rDer p 2 was performed as the protein concentration standards. (A) shows the association between the Dp concentration with the absorbance value (OD 450 nm). (B) shows the association between the Der p 2 concentration with the absorbance value (OD 450 nm). (C) shows the association between the Der p 2 concentration with the Dp concentration.

Figure 12:
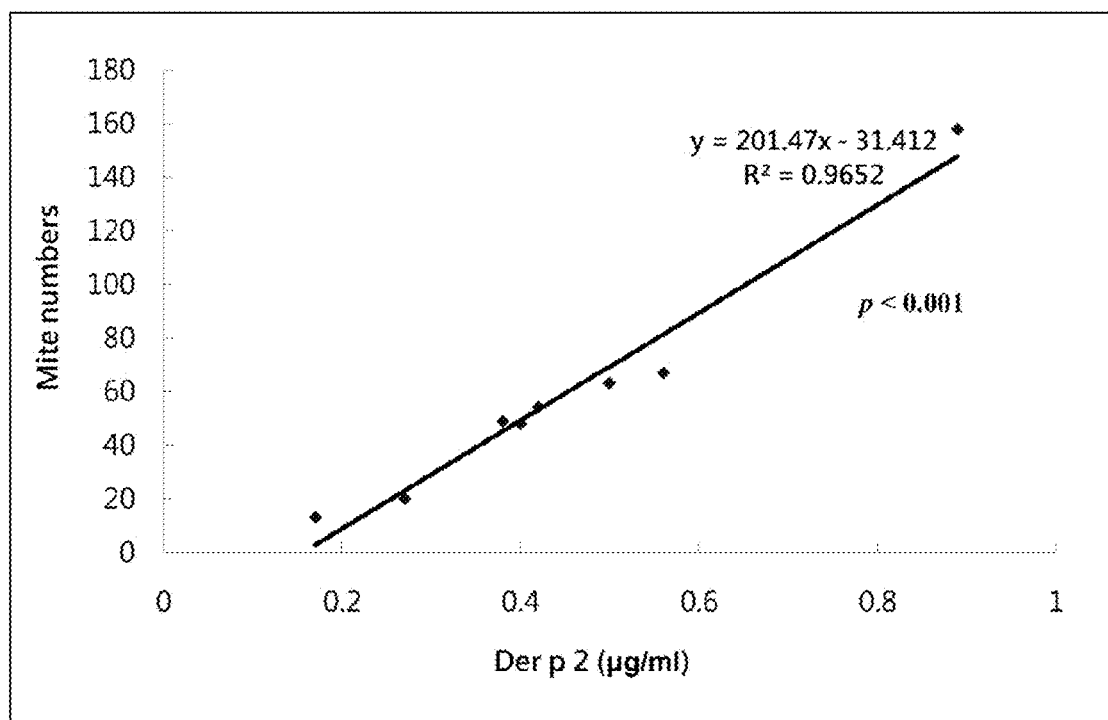

FIG. 12 shows the analyzing results of Der p 2 concentration and dust mite number. Eight dust mite samples were subjected for the association analysis of the Der p 2 concentration between the dust mite number. The concentration of Der p 2 (µg/ml) was detected by utilizing ELISA assay and the dust mite number was counted under phase contrast microscope. The association between Der p 2 concentration and dust mite number was calculated linear regression to obtain $R^2=0.9652$ ($p<0.001$).

Figure 13:
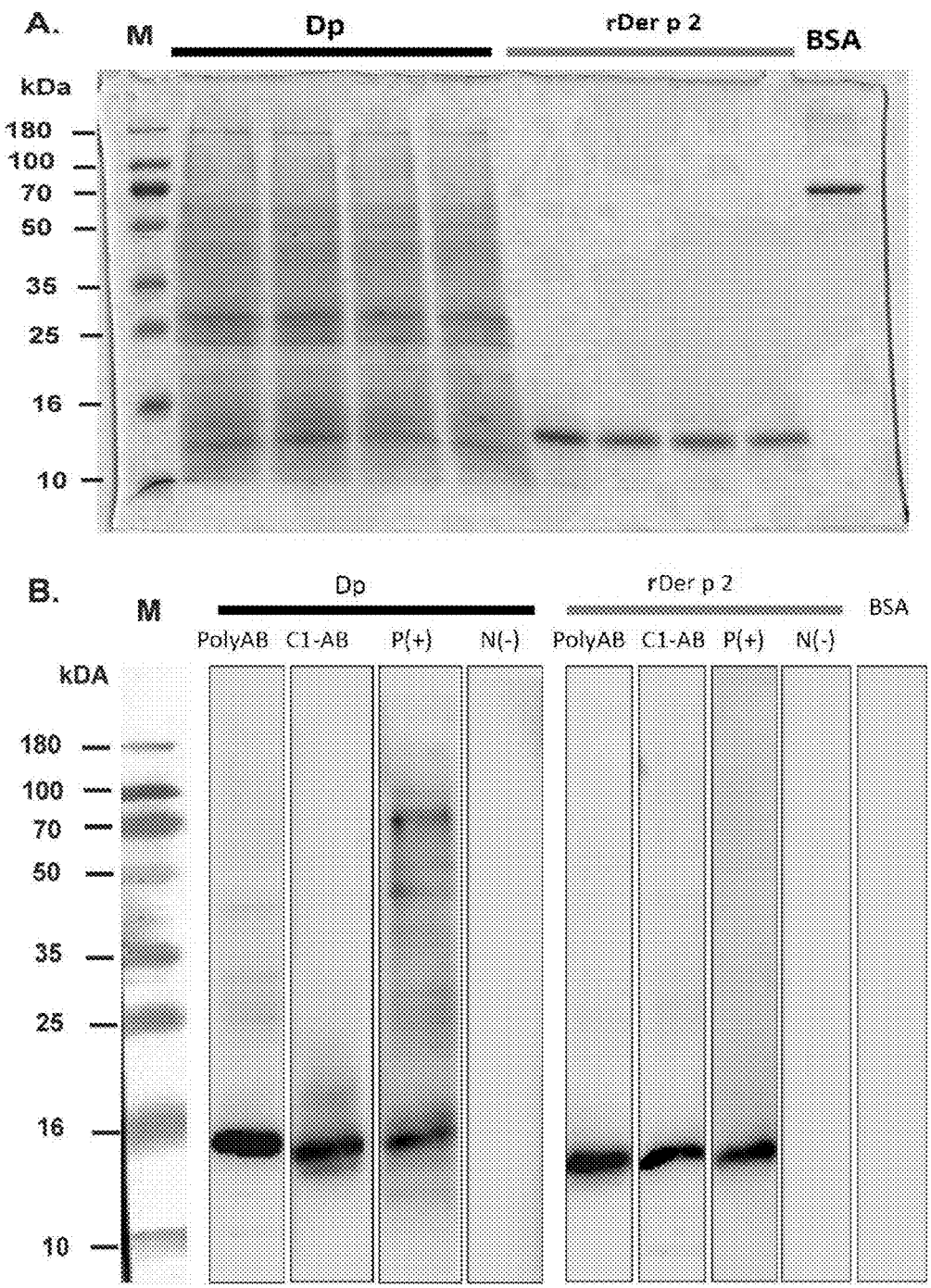

FIG. 13 reveals the protein constitution of crude extract of Dp and rDer p 2. (A) shows the result of that the protein analyzed by 12% SDS-PAGE electrophoresis and stained with Coomassie blue. M, protein marker; Dp, the crude extract of Dp; rDer p 2, recombinant protein of Der p 2; BSA, bovine serum albumin. (B) shows the result of western blot assay which were performed with different antibodies. PolyA, rabbit polyclonal antibody against Der p 2; C1-AB, mouse monoclonal antibody against Der p 2; P(+), the Dp allergy patients; N(−), healthy test.

DETAILED DESCRIPTION OF THE INVENTION

Example 1

Generation of Monoclonal Antibody Against Der p 2

Materials and Methods
1. Preparation of the Crude Extract of Dp

The dust mite is ground and suspended by PBS which contains protease inhibitor (aprotinin, 0.1 U/ml; Sigma Chemicals, St. Louis, Mo., USA) and PMSF (1 mmol/l, Sigma) for homogenization. After centrifuge at 10,000 g for 30 minutes, the supernatant is collected for dialysis in the 0.05 mol/l, pH 8.0 ammonium carbonate solution, and followed by aliquot and freeze dehydration. The concentration of the collected sample is estimated by Lowry's method with bovine serum as standard.

2. Production of Monoclonal Antibody Against Der p 2

Figure 1:
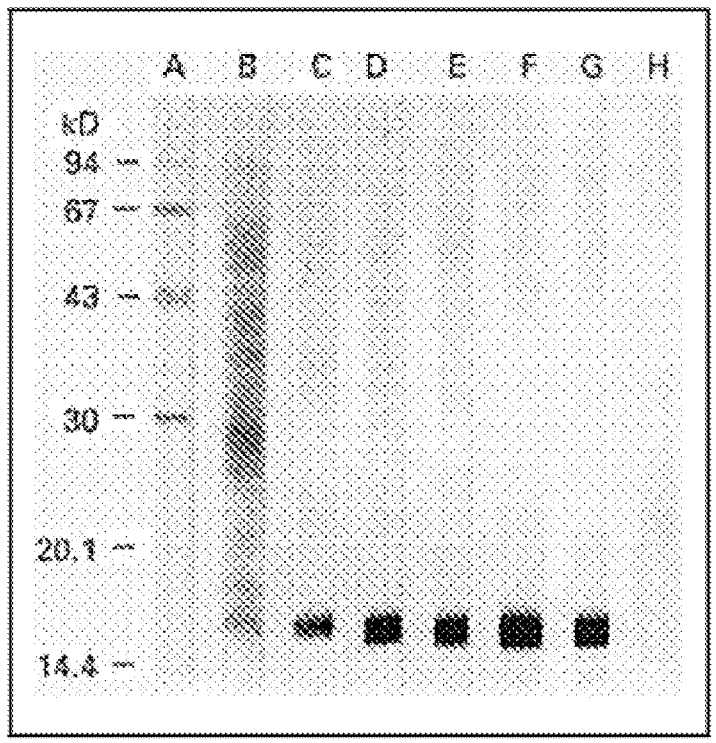
FIG. 1 represents the immunoblotting activity of monoclonal antibodies C1-C5, to detect crude extract Dp. Lane B shows that the crude extract of Dp separated by SDS-PAGE electrophoresis and transferred onto a PVDF membrane. Protein separated by SDS-PAGE electrophoresis was evident by Coomassie blue staining Lanes C-G reveal the same protein reacted with monoclonal antibodies C1-C5, respectively. Lane H shows the result of P40 antibody as negative control. Lane A shows protein markers.

The fusion protein of Der p 2 peptide fragments are expressed from the pGEX plasmid constructed by Dr. K. Y. Chua in Singapore University. The preparation procedure is examined as following: performing polymerase chain reaction (PCR) with different primer sets to obtain F1 to F16 fragments and then sub-cloning PCR products into glutathione S-transferase (GST) tagged expression plasmid and then transforming these constructs encoding the GST-fused polypeptides into *E. coli* to express the recombinant peptides. Peptide fragments in fusion protein are shown in Table 1 and the full length amino acid sequence of fusion protein is exhibited at SEQ ID NO: 1. Expression of GST fused peptide fragments were drove by Sj26 gene in pGEX vector and purified by affinity chromatography using glutathione agarose. The purified rDer p 2 is analyzed by utilizing SDS-PAGE and shown in FIG. 1. As shown in FIG. 1, the molecular weight of fusion protein, which contains the 26 kD GEX, is 42 kD.

TABLE 1

Peptide fragments of Der p 2 fusion protein

| Fragment range | Label |
|---|---|
| $S_2R$ | F1 |
| 1-32 | F2 |
| 1-69 | F3 |
| 1-76 | F4 |
| 1-84 | F5 |
| 20-32 | F6 |
| 20-45 | F7 |
| 22-45 | F8 |
| 22-76 | F9 |
| 22-129 | F10 |
| 33-61 | F11 |
| 42-84 | F12 |
| 65-84 | F13 |
| 69-115 | F14 |
| 69-129 | F15 |
| 105-129 | F16 |

The splenocytes from Balb/c mice immunized with rDer p 2 were fused with NS-1 mouse myeloma cell using polyethylene glycol (Merck, Hohenbrunn, Germany). Screen for selecting the hybridoma cells that are capable to produce antibody by utilizing ELISA, GST-Der p 2 fusion protein and GST protein. Furthermore, the cells being capable for producing monoclonal antibody against Der p 2 were selected by utilizing limit dilution and followed by sub-culture for two passages and amplification. Finally, the isotype of monoclonal antibody was identified by ELISA assay with specific antiserum as standard (Southern Biotechnology Associates, Birmingham, Ala., USA).

3. ELISA Assay

50 µl of rDer p 2, Dp and Df protein (Greer Laboratory, Lenoir, Calif., USA) were added with 0.5 µg/ml, pH 9.6 carbonate buffer in the ELISA plate. The ELISA plate was sealed and incubated at 4° C. overnight for rDer p 2, Dp and Df to attach in the pores of the polyethylene ELISA plate (Costar, Cambridge, Mass., USA).

After the incubation, discarding the rDer p 2, Dp and Df solutions and blocking the non-specific reaction with 1% skimmed milk. After milk blockage, the conditioned medium collected from hybridoma cell culture was added for incubation at 37° C. for one hour, and that is followed by wash with PBS-T buffer (PBS buffer with 0.05% Tween 20). Adding the secondary antibody (peroxidase-conjugated goat anti-mouse IgG, Bio-Rad, Peroxidase Substrate Kit 172-1064, containing 2, 2'-di-(3-ethyl benzthiazoline-6-sulfonic acid) and hydrogen peroxide) for incubation at 37° C. for 30 minutes. Detecting each well twice by ELISA reader (Titertek Multiskan, Flow Laboratories, McLean, Va., USA) at a wavelength of 415 nm to obtain the mean value of absorbance. In this analysis, the monoclonal antibody P40 against *Penicillium notatum* (from Dr. Hong-Der Shen in Taipei Veterans General Hospital) is used as the negative control. The absorbency detected from sample revealed 1.2 fold compared to the negative control was determined as positive.

4. Preparation of Der p 2 by Affinity Chromatography with Monoclonal Antibody Affinity Column The monoclonal antibodies from ascites were isolated using protein A column and coupled with CNBr-activated Sepharose 4B (Pharmacia, Uppsala, Sweden) at the concentration 4 mg/ml. After the coupling, the gel matrix further reacts with ethanolamine and was washed with sodium acetate and sodium hydrogen carbonate solution. The washed gel matrix was loaded into glass column under the production direction and 40 mg of dust mite crude extract was loaded into PBS rinsed immuno-affinity column (1.5 cm×1.5 cm) with flowing rate at 5 ml/hr. After removing the unsolved protein by PBS, two beds volume (BV) of elution fluid (0.1 mol/1 citric acid, pH 3.0) were load with flowing rate at 2 ml/hr. The protein containing solution eluted from the column was adjusted to pH 7.0 with 1 mol/l, pH 10 Tris buffer, and that was followed by adding 0.05 mol/l Ammonium bicarbonate solution, pH 8.0 for dialysis. The isolated protein from dialysis was further dehydrated by freeze dehydration and analyzed by SDS-PAGE.

5. Immunoblot Analysis

The concentration of isolated sample subjected for SDS-PAGE analysis is 200 μg in 20 μl. The Dp crude extract solution mixed with SDS-PAGE sampling buffer (2% SDS and 5% 2-mercaptoethanol) was heated at 95° C. for 5 minutes before gel electrophoresis. The protein separation by gel electrophoresis was performed in 12.5% SDS-PAGE and further transferred to PVDF membrane (0.45 μm, Millipore, Bedford, Mass., USA).

After transfer, the membrane was blocked with 1% skim milk which is prepared with TBS (20 mmol/l of Tris, 500 mmol/l of NaCl, pH 7.5). Following the blockage, the membranes were washed with TBST and incubated with first antibody, monoclonal antibodies C1 to C5, respectively. Washing the membranes with TBST and incubating with secondary antibody (alkaline phosphatase-conjugated monoclonal anti-human IgE antibodies, Pharmingen, San Diego, Calif., USA) at room temperature for 1.5 hours. After the TBST wash, the result is evident with the solution containing 0.35 mol/l BCIP (5-bromo-4-chloro-3-indyl phosphate p-toluidine salt) and 0.37 mol/l NBT (p-nitro blue tetrazolium chloride) for 30 minutes. The resulted is recorded by photography after wash with ddH$_2$O.

Results

1. Preparation of Monoclonal Antibody and Characterization of Monoclonal Antibody Five stable clones, C1 to C5, were selected upon ELISA assay and limit dilution for producing the monoclonal antibodies. The immunological characters of these monoclonal antibodies produced from C1-05 cell lines were listed in Table 2. All monoclonal antibodies containing the isotype as IgG1 with κ-light chain exhibit high activity against rper p 2 in ELISA assay. Moreover, the C1, C3 and C5 monoclonal antibodies revealed high activity to Dp in ELISA assay; in contrast, C2 and C4 antibodies revealed low activity in ELISA assay. All of these monoclonal antibodies exhibited low activity to DE Hybridoma cell lines C1 and C4 were deposited on Oct. 31, 2013, at the American Type Culture Collection (ATCC), 10801 University Boulevard, Manassas, Va. 20110 USA. The deposited stains were given the ATCC Patent Deposit Designations PTA-120688 and PTA-120687, respectively.

TABLE 2

The immuno-activity of monoclonal antibody against Der p 2 in the dust mite extract

| Monoclonal antibody | ELISA activity (absorption, 415 nm) | | | Isotype of immunoglobuin |
|---|---|---|---|---|
| | rDer p 2 | Dp extract | Df extract | |
| C1 | 2.264 | 2.594 | 0.798 | IgG1, kappa |
| C2 | 1.265 | 0.888 | 0.674 | IgG1, kappa |
| C3 | 2.441 | 2.282 | 0.598 | IgG1, kappa |
| C4 | 1.246 | 0.830 | 0.656 | IgG1, kappa |
| C5 | 2.132 | 2.056 | 0.250 | IgG1, kappa |
| P40 | 0.125 | 0.139 | 0.121 | IgG1, kappa |

The ELISA plate coated with the polypeptide of Der p 2 was performed for analyzing monoclonal antibody (0.2 μg antigen and 0.1 μg/ml C1, C3 and C5 monoclonal antibodies). The results listed in Table 3 suggest that C3 antibody recognizes F3 and F5 polypeptides; C1 and C5 antibodies recognize F5 and F15 polypeptides. Therefore, these results indicate the epitope by recognized C1 and C5 antibodies is locating in the region between 69-84 amino acids. The sequence was shown in SEQ ID NO: 2.

In addition, the monoclonal antibodies C1-C5 were subjected for western blotting to detect the Der p 2 in Dp transferred on PVDF membrane. The results shown in FIG. 1 indicate that monoclonal antibodies C1 to C5 exhibit the obvious activity to dust mite crude extract. Result of the dot blotting reveals that all monoclonal antibodies react with the protein in Dp crude extract with molecular weight of 16 kD.

TABLE 3

The peptide mapping of Der p 2 analyzed by ELISA assay to determine the epitope of these monoclonal antibodies

| Monoclonal antibody | ELISA activity (O.D. 415 nm) | | | | | |
|---|---|---|---|---|---|---|
| | S$_2$R | F3 | F5 | F9 | F15 | GEX |
| C1 | 2.606(16) | 0.331(2) | 2.474(13) | 0.305(2) | 2.532(16) | 0.151(1) |
| C2 | 2.588(16) | 2.248(13) | 2.419(13) | 1.464(9) | 1.292(8) | 0.164(1) |
| C5 | 2.490(15) | 0.504(3) | 2.454(13) | 0.434(3) | 2.516(16) | 0.162(1) |
| P40[a] | 0.162(1) | 0.176(1) | 0.192(1) | 0.168(1) | 0.160(1) | 0.188(1) |

[a]against *Penicillium notatum*, 68 kD allergenic protein

Figure 2:
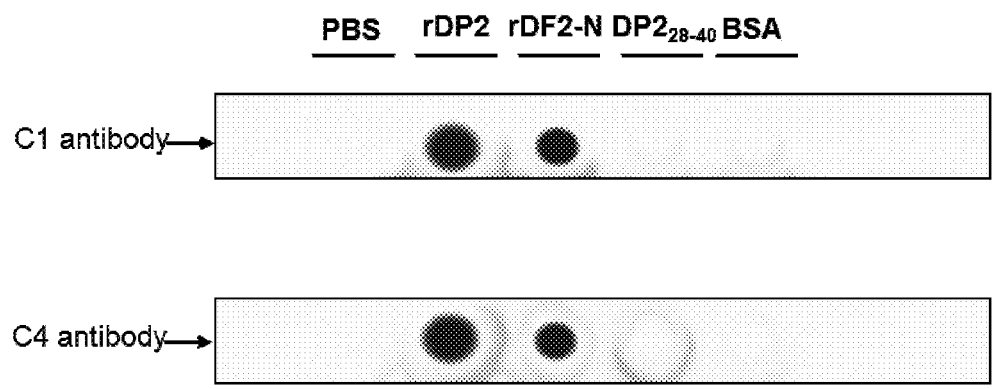
FIG. 2 shows the result of western blot analysis with monoclonal antibodies C1-C4, to detect different truncated protein of Der p 2. rDer p 2 represents the full length protein which comprises 129 amino acids; rDF1-N represents the N-terminal domain of Der p 2 which comprises 1st to 84th amino acids; DP2 28-40 represents the truncated protein of Der p 2 which comprises 28th to 40th amino acid; and the PBS and BSA is utilized as the controls.

In order to further confirm the recognized epitope of monoclonal antibody C4, we performed western blot with different truncation rDer p 2 and rDer f 2 polypeptides (prepared as described in material and method). The result shown in FIG. 2 revealed that monoclonal antibodies C1 and C4 react with DP2 and DF2-N but not with DP2 29-40, PBS and BSA control. This result suggests that the epitope recognized by monoclonal antibody C1 is locating in the N-terminal domain of Der p 2 excluding the region between 28-40 amino acids. It is consistent with our previous result that monoclonal antibody recognizes the epitope in 69-84 amino acids. The epitope recognized by monoclonal antibody C4 is locating in the N-terminal domain except for the region from 28-40 amino acids. It means the monoclonal antibody C4 recognized epitope is locating in 1-27 amino acids (the detail sequence is shown in SEQ ID NO: 3) or 41-48 amino acids (the detail sequence is shown in SEQ ID NO: 4).

2. Purification of Der p 2 Protein

Figure 3:
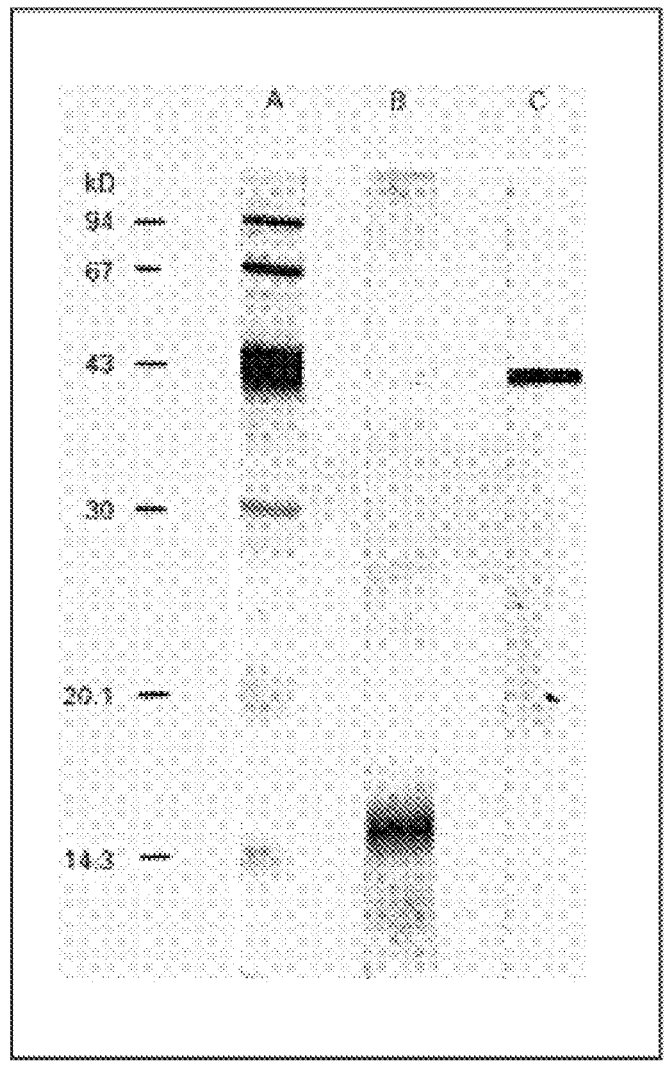
FIG. 3 shows purified Der p 2 characterized by SDS-PAGE electrophoresis. The Der p 2 was purified utilizing monoclonal antibody and glutathione-based affinity chromatography. Finally, the result was evident by silver staining Lane A is molecular weight of protein markers; lane B and C are native Der p 2 and rDer p 2, respectively.

The GST-rDer p 2 fusion protein is purified by affinity chromatography using glutathione-agarose. The purified rDer p 2 is subjected for SDS-PAGE analysis and evident by silver stain which was shown in FIG. 3. The molecular weight of fusion protein is 42 kD and the molecular weight of natural Der p 2 extracted from Dp crude extract by monoclonal antibody based affinity chromatography is 16 kD.

Example 2

Generation of Dust Mite Test Strip

Materials and Methods

1. Determination of the Mixing Ratio of Gold Solution and Monoclonal Antibody C1

First, 500 μl of Gold solution (Evernew, Nano Gold-40, gold size 25-35 nm, Yu-Shing Biotech., Ltd., Taiwan) was divided into 9 tubes. Monoclonal antibody C1 was diluted with 0.005 mol/l, pH 9.0 borate buffer for preparing the diluted C1 antibody solution with the following concentrations: 0.1 μg/ml, 0.5 μg/ml, 0.75 μg/ml, 1 μg/ml, 2.5 μg/ml, 5 μg/ml, 7.5 μg/ml and 10 μg/ml.

The aliquots of Gold solution are adjusted to pH 8.2 by using 0.1M HCl and 0.1M potassium carbonate solutions. The diluted C1 antibody solution is added into Gold solution and mixed for 5 minutes. Therein, one Gold solution without addition of diluted antibody solution was performed as negative control. All tubes were added with 500 μl of 10% NaCl and mixed well and then incubated for 2 hours. After incubation, the antibody/colloidal gold solution was analyzed by ELISA reader.

2. Labeling Monoclonal Antibody C1 with Colloidal Gold Particle 1 ml pH 8.0 gold solution adjusted by 0.1M HCl and 0.1M potassium carbonate solution were loaded into the tube, and then mixed it for 5 minutes after C1 antibody added slowly. C1 antibody/colloidal gold solution were incubated at 4° C. in the refrigerator for 2 hours and followed by centrifuge at 4° C., 13,5000 rpm for 30 minutes to discard the supernatant. To re-suspend the pellet by 0.05 M, pH 8.2 1% BSA in Tris buffer; after that, to centrifuge at 4° C., 13,5000 rpm for 30 minutes and to discard the supernatant. Finally, the pellet was re-suspended by 0.05 M, pH 8.2 Tris buffer which contains 1% BSA and 0.05% and stored at 4° C.

3. Preparation of the Test Strip for Dust Mite Assay

The inner pad (0.5 cm×5.9 cm), sample pad (0.5 cm×1.7 cm, glass fiber, Pall Life Sciences, Taiwan), binding pad (0.5 cm×0.7 cm, glass fiber, Pall Life Sciences, Taiwan), nitrocellulose membrane (0.5 cm×2.5 cm, Vivid 170™ Lateral Flow Nitrocellulose Membranes, Pall Life Sciences, Taiwan) and absorption pad (0.5 cm×1.7 cm, fibril absorption, Pall Life Sciences, Taiwan) were cropped into appropriated size. Notably, the binding pad was rinsed with solution containing 2% BSA, 2.5% sucrose, 1% Tween 20, 0.3% polyvinylpyrrolidone k30 and 0.02% $NaN_3$ over-night before cropping it. The binding pad was further baked at 37° C. and stored in dryer with appropriated size. 5 μl of C1 antibody/colloidal Gold solution was dropped on the binding pad before assemble it; after that, to be further baked at 37° C. for the following usage. 0.5 ml antibody containing solution was equally plated on rubber stamp and manually stamped on the region about 1 cm in distance between control line and test line on the cropped nitro-cellulose membrane. The antibodies distributing on control line and test line were mouse IgG and monoclonal antibody C4 with concentration at 0.9 μg/λ, respectively. The nitro-cellulose membranes stamped with antibody were further air dried in the shade for the following use.

Figure 4:
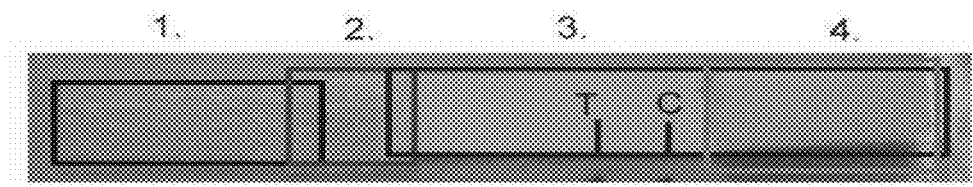
FIG. 4 is a top perspective view of dust mite detection strip. No. 1 is the sample area; No. 2 is the binding area; No. 3 is the nitro-cellulose membrane; T is the test line and C is the control line.

The above materials were assembled into the test strips for dust mite assay under the illustrations in FIG. 4. The nitrocellulose membrane was fixed on the bottom pad; the absorption pad and binding pad were placed at the left side and right side of nitrocellulose membrane. The absorption pad and binding pad were connected with nitro-cellulose membrane with connecting region about 2 mm.

4. Examination of the Test Strips for Detecting Dust Mite

The specificity, sensitivity and detection performance of these assembled test strips for detecting the environmental analytes were further verified with various samples. 100 to 200 μl of PBS dissolving the dust, rDer p 2 protein, rDer f 2 protein or PBS alone were dropped on the sample area. Furthermore, C1 antibody/colloidal Gold solution mixture was used to react with rDer p 2 protein for determining the best and minimal concentration.

Results

Figure 5:
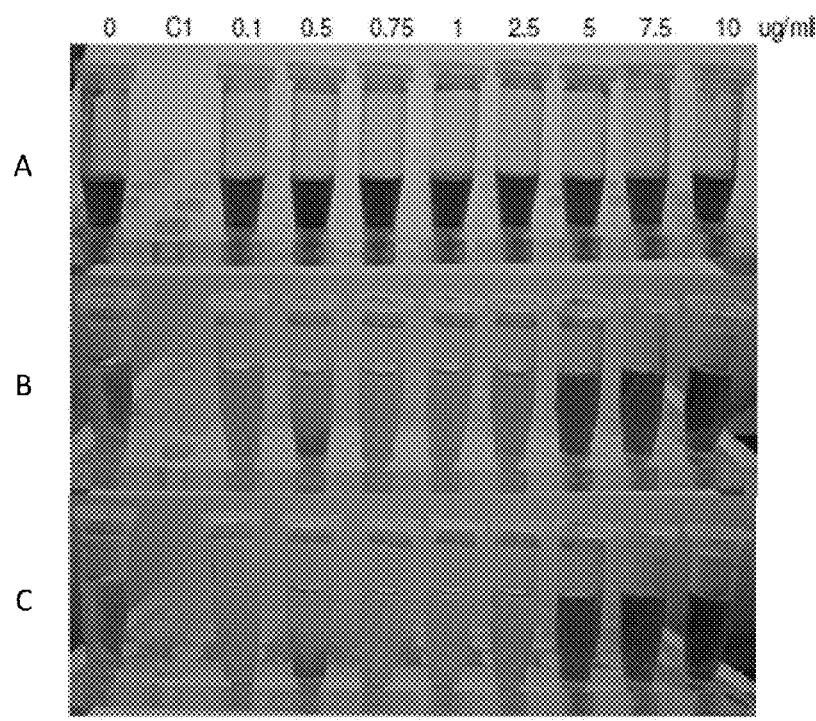
FIG. 5 shows the conjugation of colloidal gold solution performed with antibody C1 at different concentration. Line A shows antibody C1 mixed with colloidal gold solution and incubated for 5 minutes. Line B shows antibody C1/colloidal gold solution added with 500 μl, 10% NaCl solution. Line C shows the result of the mixture incubated for 2 hours.
Figure 6:
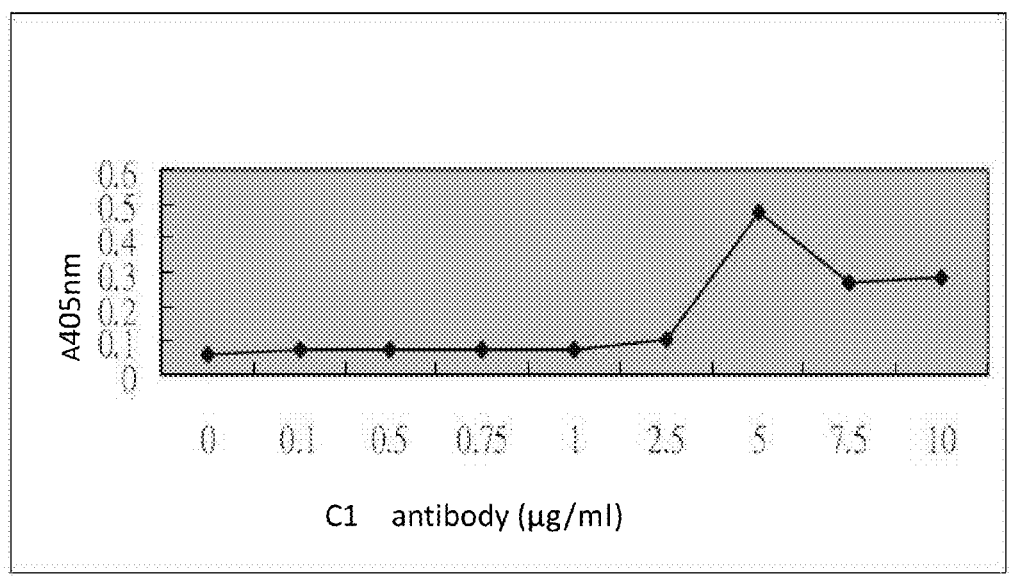
FIG. 6 shows the result to determine the best concentration of antibody C1 for reacting with colloidal gold. The absorbance value (OD 450 nm) of the mixture composed of colloidal gold with different concentration of antibody C1 were detected by ELISA reader.

1. The Most Appropriated Working Concentration of Monoclonal Antibody C1/Colloidal Gold Solution The monoclonal antibody C1 with different concentrations were added into colloidal Gold solution; hereafter, 10% NaCl was added for competing with C1 antibody. While NaCl is not able to compete with monoclonal antibody C1, which was tightly associated with colloidal gold particle, the gold particle will not precipitate. In contrast, the gold particle bound by NaCl will precipitate and result in the color solution switching into colorless solution. Therefore, the best concentration of C1 antibody could be determined while the solution switching from colorful to colorless. The results shown in FIG. 5 and FIG. 6 revealed that the colloidal gold particles precipitate and trigger the solution switch into colorless while the concentration of C1 antibody is below 2.5 μg/ml. The reduced absorbance indicates the appropriated region of concentration of C1 antibody is between 2.5 μg/ml to 10 μg/ml.

2. The Conditions for Preparing the Test Strips for Use in Dust Mite Assay

As the results shown in FIGS. 7 to 10, addition of PBS on the sample area revealed negative response in test line but showed positive response in control line while the concentration of antibody C1/colloidal gold solution were 2.5 μg/ml, 5 μg/ml, 10 μg/ml. This result indicates that the test strip could efficiently work and reveal the good sensitivity and specificity for rDer p 2 and rDer f 2. Moreover, comparing FIG. 7 and FIG. 9 could find that the positive signal on the test line was stronger while the concentration of antibody C1/colloidal gold solution was 2.5 μg/ml than 1.0 μg/ml. This difference suggests that the best working concentration of antibody C1/colloidal gold solution in the test strip is 2.5 μg/ml. The result of sensitivity test was shown in FIG. 9, in which addition of 10 µg rDer p 2 in the sample area appeared the deeper color than that addition of 1 µg rDer p 2. This result suggests that more rDer p 2 added in the sample area would evident deeper color. In addition, this test strip could detect the existence of rDer p 2 while the concentration is 1 µg that mean the great sensitivity of this test strip.

Figure 7:
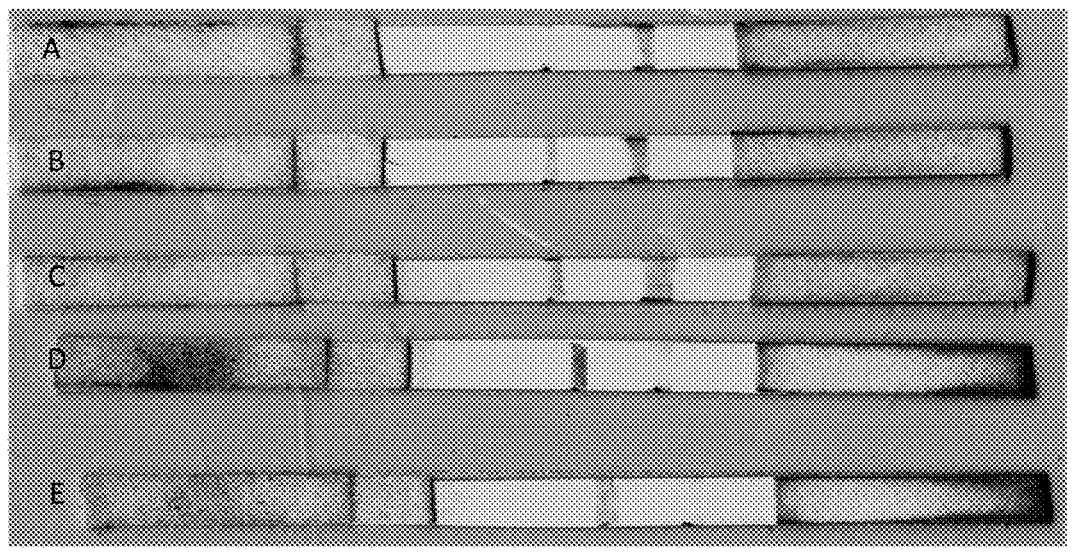
FIG. 7 shows the detection results that adding 100 μl different samples on the test strip which contains antibody C1 concentration 2.5 µg/ml within the binding area. Strip A shows that adding PBS onto the test strip. Strip B shows that 1 µg rDer p 2 containing solution added onto the test strip. Strip C shows that 10 µg rDer p 2 containing solution added onto the test strip. Strip D shows that dust samples from emergency added onto the test strip. Strip E shows that dust samples from duty room at 10 F added onto the test strip.

The result of test with environmental analyst shown in FIG. 7 and FIG. 10 revealed that the test lines were colored while added with the dust samples collected from emergency and duty room on 10 F. This result suggests that the test strip is capable for detecting the Der p 2 or Der f 2 in the dust sample.

Experiment 3

Analysis of Dust Mite Number by Elisa Assay

Materials and Methods
1. Preparation of the Crude Extract of Dust Mite Protein
The protocol for crudely extraction of dust mite protein had been described in Experiment 1.
2. Preparation of rDer p 2 Protein
The rDer p 2 protein was produced by fermentation in 1000 ml conical flask. 200 ml BMGY (Invirtogen, USA) was added into conical flask for shaking at 30° C. with oxygen concentration at 35%. The medium adjusted to pH 7.0 by 15% ammonia was added with bacteria inoculum for fermentation. Until the glycerol was depleted, 50% glycerol was sequentially added into the fermentation medium; while the added glycerol was depleted, methanol was added to induce rDer p 2 expression with the loading rate according to pH and oxygen concentration. Finally, 1 ml of fermentation medium was subjected for characterization of rDer p 2 expression by using SDS-PAGE analysis.
3. Preparations of Monoclonal and Polyclonal Antibodies Against Der p 2
The preparation of the monoclonal antibody against Der p 2 was described in Experiment 1. In the preparation of polyclonal antibody against Der p 2, the rDer p 2 was mixed with Freund's adjuvant for emulsification and subcutaneous injection into the rabbit to induce the primary immune response. Hereafter, the incomplete Freund's adjuvant (FIA, 10 ml, Sigma, St. Louis, Mo., USA) was subcutaneously injected every two weeks for three times. The serum from rabbit blood was collected and stored at −80° C.
4. ELISA Assay
Coating the monoclonal antibody C1 by adding 100 µl, pH 8.0 PBS buffer which contains 0.4 µg/ml monoclonal antibody C1 into the polyethylene ELISA plate (Costar, Cambridge, Mass., USA), and that is incubated for 3 hours. After the antibody coating, the ELISA plate was washed by PBST buffer (0.5%, Tween-20) and blocked with 1% milk at room temperature for 1 hour. The blocked plates were washed by PBST buffer and divided into two groups; the solutions containing known concentrations of rDer p 2 from 62.5 ng/ml to 1000 ng/ml were added into ELISA plate for determining the standard curve. In addition, the known concentrations of crude extracts of Dp were added as another standard group.

Both of them were incubated at room temperature for 2 hours which was followed by washing for twice. The polyclonal antibody against Der p 2 with 1000 folds dilution in PBST buffer was added and incubated at room temperature for 2 hours. After the incubation, the plate was washed twice and added with labeled antibody (peroxidase-conjugated goat anti-rabbit IgG, Bio-Rad, Peroxidase Substrate Kit 172-1064, containing 2,2-di-(3-ethyl benzthiazoline-6-sulfonic acid) and hydrogen peroxide) at 37° C. for 1 hour. ABTS containing enzyme substrate solution was adding for the peroxidase reaction. After reaction for 15 minutes, the reaction was terminated by adding 50 µl, 0.01% Sodium Azide. Finally, the absorbance value (OD 450 nm) of each wells were measured by ELISA reader (Sunrise, TECAN, Switzerland).
5. Collection of Dust for Detecting the Dust Mite Number
Random sampling was performed at eight different positions in the hospital every month from April 2010 to March 2011 (the eight positions including six on the carpets in meeting room and library, and two positions on the mattress in the duty room). The dust was collected by vacuum cleaner from the region about one meter square in the sampling position for one minute for the following assay.

0.1 g dust of each sample was mixed with 25 ml NaCl solution by shacking and incubation for 10 minutes. After the mixed solution flowing through the filter paper with 45 µm pore, the residuum on the filter paper was flashed on the culture dish for counting the dust mite number under phase contrast microscopy (Olympus SZ-PT, Japan). Furthermore, the dust mites were transferred into polyvinyl alcohol on the slide by micro-needle, and mounted by cover slide. The species and cellularity of these dust mites were verified and counted.

Results
1. The Dust Mite Number in the Dust
The statistic result of the dust mite number of the eight samples collected from different sampling positions in Taichung Veterans General Hospital was showed in Table 4. The dust mite in position C1 to C6 were collected from the carpets; in addition, the dust mite in position M1 and M2 were collected from mattress.

TABLE 4

| | The number of dust mites in the dust | | | | | | | | | | | |
|---|---|---|---|---|---|---|---|---|---|---|---|---|
| Dust mite number/0.1 g | April 2010 | May | June | July | August | September | October | November | December | January 2011 | February | March |
| C1 | 16 | 8 | 13 | 9 | 11 | 15 | 9 | 6 | 11 | 13 | 11 | 7 |
| C2 | 8 | 19 | 12 | 15 | 19 | 8 | 7 | 11 | 17 | 9 | 13 | 14 |
| C3 | 18 | 6 | 9 | 4 | 26 | 19 | 14 | 8 | 13 | 12 | 8 | 16 |
| C4 | 8 | 2 | 4 | 8 | 6 | 4 | 11 | 10 | 9 | 15 | 7 | 8 |
| C5 | 11 | 16 | 18 | 16 | 10 | 7 | 10 | 9 | 6 | 17 | 11 | 12 |
| C6 | 9 | 16 | 14 | 8 | 14 | 12 | 9 | 19 | 15 | 8 | 13 | 18 |
| M1 | 60 | 20* | 54 | 67 | 37 | 32 | 25 | 68 | 55 | 49 | 35 | 58 |
| M2 | 64 | 48 | 158 | 103 | 48 | 42 | 37 | 59 | 69 | 63 | 49 | 55 |

C: carpet;
M: mattress;
*The dust was collected after the clearance of the mattress and room.

2. Analysis by ELISA Detection Platform

The standard curves of the ELISA assay platforms constituted by monoclonal antibody C1 and polyclonal antibody against Der p 2 were shown in FIGS. 11A & 11B. In addition, the standard curves combined with statistic result were shown in FIG. 11C that reveals high association ($R^2=0.9715$) between these two curves. The FIG. 11C also suggested that there is 0.0544 g Der p 2 existing in 1 g crude extract of Dp.

3. The Association Between Dust Mite Number and Concentration of Der p 2

Eight samples randomly selected from the results showed in Table 4 were subjected for ELISA assay to determine the association between dust mite number and Der p 2 that were shown in Table 5. Consistently, the statistic result suggests that the concentration of Der p 2 analyzed by ELISA assay exhibits high association ($R^2=0.9652$) with the dust mite number analyzed upon manual counting under microscopy. Furthermore, western blot was performed with specific antibodies against Der p 2 used in ELISA platform (including monoclonal antibody and polyclonal antibody against Der p 2) to confirm the quality of this ELISA platform. The results shown in FIGS. 13A & 13B revealed that the monoclonal antibody and polyclonal antibody against Der p 2 exhibit high specificity to the crude extract of Der p 2 or rDer p 2.

TABLE 5

ELISA assay results and corresponding dust mite number, concentration of crude extract of Dp and Der p 2.

| | AU# (OD450 nm) | Dust mite number (n) | Dp (µg/ml) | Der p 2 (µg/ml) | Dp (µg/g dust) | Der p 2 (µg/g dust) |
|---|---|---|---|---|---|---|
| June 2010 | | | | | | |
| M1 | 0.093 | 54 | 15.92 | 0.42 | 6.37 | 0.17 |
| M2 | 0.197 | 158 | 36.19 | 0.89 | 14.48 | 0.36 |
| July 2010 | | | | | | |
| M1 | 0.124 | 67 | 21.96 | 0.56 | 8.78 | 0.22 |
| May 2010 | | | | | | |
| M1 | 0.060 | 20 | 9.86 | 0.27 | 3.94 | 0.11 |
| M2 | 0.088 | 48 | 15.19 | 0.40 | 6.08 | 0.16 |
| January 2011 | | | | | | |
| C1 | 0.040 | 13 | 5.59 | 0.17 | 2.24 | 0.07 |
| M1 | 0.085 | 49 | 14.36 | 0.38 | 5.74 | 0.15 |
| M2 | 0.112 | 63 | 19.62 | 0.50 | 7.85 | 0.20 |

AU (absorbance unit is OD450 nm)

However, the above-mentioned specification is only for detailed description with the examples of the invention and shall not be construed as a limitation of the scope of the invention. Thus, any modification or change without departing from the characteristics of the invention or any equivalent thereof shall be included in the scope of the invention defined in the following claims.

What is claimed is:

1. A monoclonal antibody that specifically binds to a epitope of Der p 2, wherein said monoclonal antibody binds to the same epitope as the monoclonal antibody produced by hybridoma cell line C1 (ATCC Patent Deposit Designation PTA-120688) and has the same antigen binding site as the monoclonal antibody produced by hybridoma cell line C1.

2. The monoclonal antibody of claim 1, wherein said monoclonal antibody is produced by said hybridoma cell line C1.

3. The monoclonal antibody of claim 1, wherein said monoclonal antibody is of the IgG1 subclass and comprises a kappa light chain.

4. The monoclonal antibody of claim 1, wherein the amino acid sequence of said epitope is SEQ ID NO: 2.

5. The monoclonal antibody of claim 1, wherein said monoclonal antibody binds to a Der p 2 having a molecular weight of 16 kD.

6. An immortalized cell line which produces a monoclonal antibody, wherein said monoclonal antibody specifically binds to the same epitope of Der p 2 as the monoclonal antibody produced by hybridoma cell line C1 (ATCC Patent Deposit Designation PTA-120688) and has the same antigen binding site as the monoclonal antibody produced by hybridoma cell line C1.

7. The immortalized cell line of claim 6, wherein said immortalized cell line is said hybridoma cell line C1.

8. The immortalized cell line of claim 6, wherein said monoclonal antibody is of the IgG1 subclass and comprises a kappa light chain.

9. The immortalized cell line of claim 6, wherein the amino acid sequence of said epitope is SEQ ID NO: 2.

10. The immortalized cell line of claim 6, wherein the Der p bound by said monoclonal antibody has the molecular weight of 16 kD.

* * * * *

SEQUENCE LISTING

```
<160> NUMBER OF SEQ ID NOS: 4

<210> SEQ ID NO 1
<211> LENGTH: 129
<212> TYPE: PRT
<213> ORGANISM: Dermatophagoides pteronyssinus

<400> SEQUENCE: 1

Arg Asp Gln Val Asp Val Lys Asp Cys Ala Asn His Glu Ile Lys Lys
1               5                   10                  15

Val Leu Val Pro Gly Cys His Gly Ser Glu Pro Cys Ile Ile His Arg
            20                  25                  30

Gly Lys Pro Phe Gln Leu Glu Ala Leu Phe Glu Ala Asn Gln Asn Ser
        35                  40                  45

Lys Thr Ala Lys Ile Glu Ile Lys Ala Ser Ile Asp Gly Leu Glu Val
    50                  55                  60

Asp Val Pro Gly Ile Asp Pro Asn Ala Cys His Tyr Met Lys Cys Pro
65                  70                  75                  80

Leu Val Lys Gly Gln Gln Tyr Asp Ile Lys Tyr Thr Trp Asn Val Pro
                85                  90                  95

Lys Ile Ala Pro Lys Ser Glu Asn Val Val Val Thr Val Lys Val Met
            100                 105                 110

Gly Asp Asn Gly Val Leu Ala Cys Ala Ile Ala Thr His Ala Lys Ile
```

-continued

```
                 115                 120                 125
Arg

<210> SEQ ID NO 2
<211> LENGTH: 16
<212> TYPE: PRT
<213> ORGANISM: Dermatophagoides pteronyssiuns

<400> SEQUENCE: 2

Ile Asp Pro Asn Ala Cys His Tyr Met Lys Cys Pro Leu Val Lys Gly
1               5                   10                  15

<210> SEQ ID NO 3
<211> LENGTH: 29
<212> TYPE: PRT
<213> ORGANISM: Dermatophagoides pteronyssiuns

<400> SEQUENCE: 3

Arg Asp Gln Val Asp Val Lys Asp Cys Ala Asn His Glu Ile Lys Lys
1               5                   10                  15

Val Leu Val Pro Gly Cys His Gly Ser Glu Pro Cys Ile
            20                  25

<210> SEQ ID NO 4
<211> LENGTH: 44
<212> TYPE: PRT
<213> ORGANISM: Dermatophagoides pteronyssiuns

<400> SEQUENCE: 4

Leu Phe Glu Ala Asn Gln Asn Ser Lys Thr Ala Lys Ile Glu Ile Lys
1               5                   10                  15

Ala Ser Ile Asp Gly Leu Glu Val Asp Val Pro Gly Ile Asp Pro Asn
            20                  25                  30

Ala Cys His Tyr Met Lys Cys Pro Leu Val Lys Gly
            35                  40
```